(12) United States Patent
Garcia et al.

(10) Patent No.: US 7,098,362 B2
(45) Date of Patent: Aug. 29, 2006

(54) PROCESSES FOR THE PREPARATION OF GABAPENTIN

(75) Inventors: Rafael Garcia, Barcelona (ES); Johannes Ludescher, Breitenbach (AT); Jordi Rifa, Sant Quirze de Bersora/Barcelona (ES); José Diago, Granollers/Barcelona (ES)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 11/184,432

(22) Filed: Jul. 19, 2005

(65) Prior Publication Data
US 2006/0020034 A1    Jan. 26, 2006

(30) Foreign Application Priority Data
Jul. 20, 2004 (GB) ................. 0416228.5

(51) Int. Cl.
C07C 61/08 (2006.01)
A01N 37/12 (2006.01)

(52) U.S. Cl. .................... 562/507; 514/561

(58) Field of Classification Search ............... 562/507; 514/561
See application file for complete search history.

(56) References Cited

U.S. PATENT DOCUMENTS

| | | | | |
|---|---|---|---|---|
| 4,024,175 | A | 5/1977 | Satzinger et al. | 260/468 |
| 5,319,135 | A | 6/1994 | Jennings et al. | 562/507 |
| 5,362,883 | A | 11/1994 | Jennings et al. | 548/408 |
| 5,693,845 | A | 12/1997 | Jennings et al. | 558/431 |
| 6,528,682 | B1 * | 3/2003 | Bosch Llado et al. | 562/507 |
| 2003/0009055 | A1 | 1/2003 | Velardi et al. | 562/507 |

FOREIGN PATENT DOCUMENTS

| | | |
|---|---|---|
| EP | 0 340 677 | 11/1989 |
| EP | 0 414 262 | 2/1991 |
| EP | 0 414 274 | 2/1991 |
| EP | 0 432 504 | 6/1991 |
| WO | 98/28255 | 7/1998 |
| WO | 99/18063 | 4/1999 |
| WO | 00/01660 | 1/2000 |
| WO | 00/64857 | 11/2000 |
| WO | 02/34709 | 5/2002 |
| WO | 02/074727 | 9/2002 |
| WO | 03/070683 | 8/2003 |
| WO | 03/089403 | 10/2003 |

OTHER PUBLICATIONS

The Merck Index, Title: Gabapentin, Whitehouse Station, New Jersey, website: https://themerckindex.cambridgesoft.com (Aug. 30, 2005).
Greene et al., "Protective Groups in Organic Synthesis, $2^{nd}$ Edition", John Wiley & Sons, Inc., New York, pp. 68-73 and 377 (1991).

* cited by examiner

Primary Examiner—Samuel Barts
Assistant Examiner—Lalitha Nagubandi
(74) Attorney, Agent, or Firm—John D. Thallemer

(57) ABSTRACT

The present invention relates to new processes for the preparation of gabapentin by the desilylation of a silylated gabapentin or by the silylation-desilylation of an acid addition salt of gabapentin with a silylating agent.

11 Claims, No Drawings

PROCESSES FOR THE PREPARATION OF GABAPENTIN

FIELD OF THE INVENTION

The present invention relates to new processes for the preparation of gabapentin by the desilylation of a silylated gabapentin or by the silylation-desilylation of an acid addition salt of gabapentin with a silylating agent. More particularly the invention relates to a process for the preparation of Gabapentin form II.

BACKGROUND OF THE INVENTION

Gabapentin of formula (1), is the generic name of a well-known anticonvulsant agent, described for example in the Merck Index, 13$^{th}$ Edition (2001), page 767 (4342).

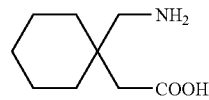

(1)

1-(aminomethyl)-1-cyclohexane acetic acid (Gabapentin) has been used for the treatment of cerebral disorders such as epilepsy, hypokinesia, faintness attacks and brain trauma. Commercially available gabapentin currently on the market is an anhydrous crystalline form that, hereinafter, will be referred to as form II. Several other gabapentin polymorphic forms have been described in the literature, being the more important gabapentin monohydrate (form I, EP0340677) and gabapentin form III (WO98/28255).

Many processes for the preparation of gabapentin have been hitherto described in the literature.

For example, WO99/18063 discloses a multi step synthesis wherein gabapentin of formula (1) is obtained as a final product after the catalytic hydrogenation of chemical intermediates comprising a cyano group. The involvement of cumbersome multi-step synthesis, high pressure hydrogenation and use of cyanides or other toxic reagents make these processes difficult from the technical point of view.

However, most of the reported synthesis proceed through the intermediate of an acid addition salt of gabapentin which is finally neutralized to gabapentin of formula (1).

This neutralization can be carried out with the use of ion exchange columns (U.S. Ser. No. 03/009,055, WO02/074727, U.S. Pat. Nos. 5,319,135, 5,693,845, 5,362,883, EP0432504, EP0414274, EP0414262, WO03/089403, WO02/034709, WO00/064857, U.S. Pat. No. 4,024,175, and EP0340677). In this neutralization process, solutions of acid addition salts of gabapentin in water or in short chain alcohols are eluted through ion exchange columns to get solutions of gabapentin of formula (1) in a free amino acid form. The rather long elution time needed, the large volumes of water or alcohols that should be evaporated and the need to introduce a rinse of the column in order to maintain the exchange capacity make these processes difficult to scale up.

In other cases, the neutralization can be carried out with the use of a base (WO98/28255, U.S. Pat. Nos. 5,362,883, and 53,191,385).

WO98/028255 discloses a process for preparing gabapentin of formula (1) consisting of dissolving gabapentin hydrochloride in a solvent and neutralizing it by addition of an amine in solution, said solvent being chosen in such a way that the amine hydrochloride formed during the neutralization is more soluble therein than the anhydrous gabapentin. In accordance with WO98/028255, a new form of anhydrous gabapentin, named form III, is prepared in the neutralization process. It is necessary to reprocess this form III by digestion or recrystallization in another solvent, to be able to prepare the pharmaceutical grade anhydrous gabapentin base, which is named form II in WO98/028255. This process does not require the use of ion exchange resins, but has the drawback that, unless closely adjusted amounts of neutralizing amine are used, the product obtained may be contaminated with appreciable amounts of the amine used in the neutralization and which have to be removed subsequently from the end product, by additional purification steps. Furthermore, this process also requires the preparation of an intermediate, the so-called form III, which has to be reprocessed, with the corresponding decrease in yield and productivity.

U.S. Pat. Nos. 5,362,883 and 5,319,135 disclose that gabapentin among other products, may be prepared from the acid addition salts thereof, e.g., from the hydrochloride, by their neutralization with a long list of bases, among which there are the free amines, sodium hydroxide, potassium hydroxide, calcium hydroxide and basic ion exchange resins. However, the examples (Method F) of said patents only describe the use of the said resins for neutralizing aqueous solutions of gabapentin hydrochloride, i.e. a method corresponding with the one already described for example in the aforementioned patent EP0340677. If sodium hydroxide, potassium hydroxide or calcium hydroxide are used as neutralizing agent, the obtained gabapentin is contaminated with mineral salts insoluble in organic solvents. The only way of getting rid of these mineral salts is by adding water, but then the yield decreases due to the high solubility of gabapentin in water. In addition, since water is used, the polymorph of gabapentin which is obtained is the monohydrate (Form I).

Finally, WO00/001660 discloses a process for the preparation of gabapentin in anhydrous form (i.e. form II), without using monohydrate gabapentin (i.e. form I), by treating an aqueous suspension of gabapentin with 2-methoxyethanol or 2-ethoxyethanol and crystallizing with an alcoholic solvent. In this process, the isolation of gabapentin monohydrate is avoided since water is eliminated by azeotropic distillation, however big volumes of water should be distilled in order to be removed.

There is, therefore, a need for developing alternative processes for the preparation of pharmaceutical grade gabapentin, allowing the industrial preparation of this product to be simplified and, therewith, the production costs to be reduced.

SUMMARY OF THE INVENTION

The present invention provides new and straightforward processes for the preparation of gabapentin by the desilylation of a silylated gabapentin or by the silylation-desilylation of the acid addition salt of gabapentin with a silylating agent.

Those processes avoid the several drawbacks associated with the aforementioned processes; multistep synthesis, isolation of intermediates (monohydrate or crude gabapentin), evaporation of larges volumes of solvents, and provide pharmaceutical grade gabapentin.

The use of silylating agent during the silylation step according to the invention brings the advantage to avoid or limit the cyclization of gabapentin to its corresponding lactam.

DESCRIPTION OF THE INVENTION

A first object of the present invention is related to a two step process for the preparation of gabapentin of formula (1),

(1)

comprising the following steps:
(b) desilylation of a silylated gabapentin of formula (2)

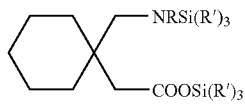
(2)

wherein R represents an hydrogen atom or a $Si(R')_3$ group and R' represents a $C_1$–$C_4$ alkyl group, by adding a protic solvent or a mixture thereof and,
(c) recovering the gabapentin of formula (1) from the reaction mixture.

The desilylation step (b) corresponds to the cleavage of the silyl group of the silylated gabapentin of formula (2) to give the gabapentin of formula (1). Desilylation step (b) can be carried out by any conventional technique well known in the art (such as T. W. Greene and P. G. Wuts in "Protective groups in organic synthesis", $2^{nd}$ Edition) by adding a protic solvent to the silylated gabapentin of formula (2).

Preferred protic solvents used in the desilylation step (b) are those described in the literature for desilylation reaction and are especially selected from the group consisting of water and C1–C6 alkyl alcohol or a mixture thereof. Preferred C1–C6 alkyl alcohols include, but are not limited to methanol, ethanol, 2-propanol (isopropanol), butanol (such as n-butanol, isobutanol, and t-butanol) and isoamyl alcohol (isopentanol) or a mixture thereof. Especially preferred protic solvent (desilylating agent) is methanol, isopropanol, water or a mixture of thereof.

Good results can be obtained when the temperature of desilylation step (b) is chosen from 25° C. to 85° C. Preferred temperatures for desilylation step (b) is chosen from 10° C. to 70° C.

Preferably, the desilylation step according to the first object of the invention is preceded by a silylation step comprising the silylation of an acid addition salt of gabapentin of formula (3) with a silylating agent.

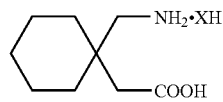
(3)

Accordingly, a second object of the present invention is related to a three step process for the preparation of gabapentin in anhydrous or hydrated form of formula (1)

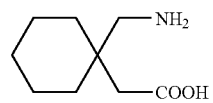
(1)

comprising the following steps:
(a) silylation of an acid addition salt of gabapentin of formula (3)

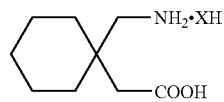
(3)

wherein XH represents a mineral acid or a strong organic acid, with a silylating agent in an anhydrous aprotic polar solvent or a mixture thereof to give a silylated gabapentin of formula (2)

(2)

wherein R represents an hydrogen atom or a $Si(R')_3$ group and R' represents a C1–C4 alkyl group and,
(b) desilylation of the silylated gabapentin of formula (2) by adding a protic solvent or a mixture thereof and,
(c) recovering the gabapentin of formula (1) from the reaction mixture.

Preferably, after step (a) and before step (b) the reaction mixture is filtered in order to remove insoluble salts formed during the silylation reaction.

After mixing the silylating agent and the acid addition salt of gabapentin of formula (3), the trialkylsilylderivative of formula (2) is formed immediately. Good results can be obtained when the temperature of silylation step (a) is chosen from −40° C. to +80° C. Preferred temperatures for silylation step (a) are from −25° C. to +10° C.

Silylation agents are well known in the art (e.g. T. W. Greene and P. G. Wuts in "Protective groups in organic synthesis", $2^{nd}$ Edition). Preferred silylation agent is selected from the group consisting of N,N-bis(trimethylsilyl)acetamide, N,N-diethyl-N-(trimethylsilyl)amine, N,N-dimethyl-N-(trimethylsilyl)amine, N,N-diisopropyl-N-(trimethylsilyl)amine and N-(trimethylsilyl)imidazole, which are commercially available. Especially preferred silylation agent is N,N-diethyl-N-(trimethylsilyl)amine.

Preferred anhydrous aprotic polar solvents used in the silylation step (a) are those described in the literature for silylation reaction, such as T. W. Greene and P. G. Wuts in "Protective groups in organic synthesis", $2^{nd}$ Edition, and are especially selected from the group consisting of N,N-dimethylformamide, N,N-dimethylacetamide, acetonitrile or tetrahydrofuran or a mixture thereof.

Preferred mineral acid is selected from the group consisting of hydrochloric acid, sulfuric acid, nitric acid, phosphoric acid, hydrobromic acid. The commercially available gabapentin hydrochloride is preferred as starting material according to the second object of the invention.

Other acid addition salts of gabapentin of formula (3) can be prepared for example according to WO03/089403 or from gabapentin monoamide as described in WO 03/070683.

Preferred strong organic acid is selected from the group consisting of paratoluensulphonic acid and formic acid.

Preferably, the ratio between the acid addition salt of gabapentin of formula (3) and the silylating agent is chosen from 1:10 to 1:2, especially preferred ratio is 1:5.

The gabapentin of formula (1) prepared according to the invention may be recovered by methods known in the art, such as recrystallization or slurrying the gabapentin in a suitable organic solvent or a mixture thereof. Preferably, the gabapentin is recrystallized in alkyl alcohol or a mixture thereof. Preferred alcoholic solvents used in the recovering step (c) are C1–C6 alkyl alcohols solvents or mixture thereof. Preferred C1–C6 alkyl alcohols include, but are not limited to, methanol, ethanol, 2-propanol (isopropanol), butanol (such as n-butanol, isobutanol, and t-butanol) and isoamyl alcohol (isopentanol) or a mixture thereof. Most preferred C1–C6 alkyl alcohols used in the recovering step (c) are methanol, ethanol, isopropanol or a mixture thereof.

According to the invention gabapentin of formula (1) can be prepared in an anhydrous or hydrated form. Preferably, the gabapentin of formula (1) is recovered from the reaction mixture and crystallized by adding methanol, isopropanol or a mixture thereof.

In order to isolate the gabapentin polymorphic form II (commercially available form) methanol, isopropanol or a mixture thereof are particularly preferred in the recovering step (c) according to the invention.

Any other polymorph or hydrate of gabapentin of formula (1) can also be isolated as end product by using specific ratio of organic solvents or mixture thereof as disclosed in the prior art. For example gabapentin form III is isolated if the product is crystallized from isopropanol and gabapentin monohydrate could be obtained if water is used.

A preferred process according to the invention giving excellent results is the following:

(a) gabapentin hydrochloride solid or dissolved or suspended in anhydrous N,N-dimethylformamide or anhydrous acetonitrile or a mixture thereof is added dropwise on a mixture of anhydrous N,N-diethyl-N-(trimethylsilyl)amine and anhydrous N,N-dimethylformamide or anhydrous acetonitrile at a temperature from −25° C. to 0° C., stirring is kept for less than one hour and the precipitated diethylamine hydrochloride is filtered off, (b) the solution of the resulting gabapentin trialkylsilyl derivative is desilylated by pouring on hot methanol, (c) gabapentin of formula (1) is recovered from the reaction mixture and is finally crystallized by adding isopropanol, methanol or a mixture thereof and cooling down.

Following this technique gabapentin form II is obtained with a yield of about 80%. From the mother liquors a second crop can be isolated following any conventional procedure and giving an overall yield of 90%. Good results are obtained by isolating gabapentin hydrochloride from the mother liquors.

This invention will be better understood from the Examples that follow. However, these examples illustrate but do not limit the invention. Those skilled in the art will readily appreciate that the specific process and results discussed are merely illustrative of the invention as described more fully in the claims that follow thereafter.

The following non-limiting examples illustrate further aspects of the invention.

EXAMPLE 1

Preparation of gabapentin form II from gabapentin hydrochloride through silylation with N,N-diethyl-N-(trimethylsilyl)amine in N,N-dimethylformamide.

A solution of 10.00 g of gabapentin hydrochloride in 20 mL of N,N-dimethylformamide was slowly added to 31.50 g of N,N-diethyl-N-(trimethylsilyl)amine cooled between 0 and −5° C. while keeping stirring and temperature. The dropping funnel was washed with 5 mL of N,N-dimethylformamide and the washing was added to the reaction mixture. The resulting suspension was stirred for 30 minutes. The diethylamine hydrochloride formed was filtered off and washed with 5 mL of N,N-dimethylformamide. The filtrate and wash solutions were combined and added to 85 mL of methanol at 60° C. To the resulting solution 170 mL of isopropylalcohol were added while maintaining the temperature. The resulting solution was seeded with gabapentin form II, cooled down to room temperature and maintained at this temperature for at least 1 hour. The mixture is cooled then to −10° C. and maintained at this temperature for at least 2 additional hours. The precipitate was collected by filtration, washed with 15 mL of a mixture of methanol and isopropanol (1:2) cooled at −10° C., and dried at 50° C. for two hours to get 6.0 g of gabapentin form II (yield 74%). Assay by HPLC: higher than 99%. Lactam content below 0.1%. From the mother liquors a second crop of gabapentin (for example in form of gabapentin hydrochloride) can be isolated giving a overall yield higher than 90%.

EXAMPLE 2

Preparation of gabapentin form II from gabapentin hydrochloride through silylation with N,N-diethyl-N-(trimethylsilyl)amine in acetonitrile.

10.00 g of gabapentin hydrochloride was slowly added on a mixture of 30.7 g of N,N-diethyl-N-(trimethylsilyl)amine and 8.3 mL of acetonitrile cooled between −20° C. and −25° C. while keeping stirring and temperature. The resulting suspension was stirred for 20 minutes at 0° C. The diethylamine hydrochloride formed was filtered off and washed with 5 mL of acetonitrile. The filtrate and wash solutions were combined and added to 66 mL of methanol at 60° C. to 65° C. To the resulting solution 133 mL of isopropylalcohol were added while maintaining the temperature. The resulting solution was seeded with gabapentin form II, cooled down to room temperature and maintained at this temperature for at least 1 hour. The mixture is cooled then to −10° C. and maintained at this temperature range for at least 2 additional hours. The precipitate was collected by filtration, washed with 15 mL of a mixture of methanol and isopropanol (1:2) cooled at −10° C., and dried at 50° C. for two hours to get 4.6 g of gabapentin form II (yield 56%). Assay by HPLC: higher than 99%. Lactam content below 0.1%. From the mother liquors a second crop of gabapentin (for example, in form of gabapentin hydrochloride) can be isolated giving an overall yield higher than 90%.

What the invention claimed is:

1. A process for preparing gabapentin form of formula (1),

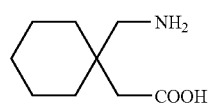

(1)

comprising the following steps:
(b) desilylation of a silylated gabapentin of formula (2)

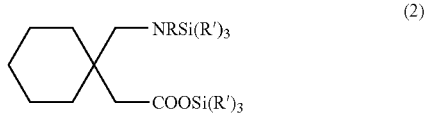

wherein R represents an hydrogen atom or a Si(R')$_3$ group and R' represents a C$_1$–C$_4$ alkyl group, by adding a protic solvent or a mixture thereof and,
(c) recovering the gabapentin of formula (1) from the reaction mixture.

2. A process according to claim 1, further comprising step (b) being preceded by a silylation step (a) comprising the silylation of an acid addition salt of gabapentin of formula (3)

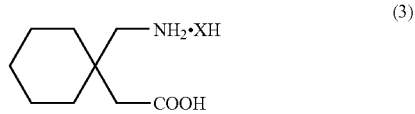

wherein XH represents a mineral acid or a strong organic acid, with a silylating agent in an anhydrous aprotic polar solvent or a mixture thereof to give a silylated gabapentin of formula (2)

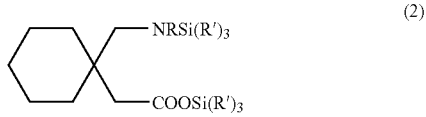

wherein R represents an hydrogen atom or a Si(R')$_3$ group and R' represents a C$_1$–C$_4$ alkyl group.

3. A process according to claim 2, wherein the acid addition salt of gabapentin of formula (3) is gabapentin hydrochloride.

4. A process according to claim 1, wherein the protic solvent of desilylation step (b) is selected from the group consisting of water and C$_1$–C$_6$ alkylalcohol or a mixture thereof.

5. A process according to claim 4, wherein the protic solvent of desilylation step (b) is selected from the group consisting of water, methanol, isopropanol or a mixture thereof.

6. A process according to claim 2, wherein the reaction mixture is filtered after step (a) and before step (b).

7. A process according to claim 2, wherein the silylating agent of silylation step (a) is selected from the group consisting of N,N-bis(trimethylsilyl) acetamide, N,N-diethyl-N-(trimethylsilyl)amine, N,N-dimethyl-N-(trimethylsilyl)amine, N,N-diisopropyl-N-(trimethylsilyl)amine and N-(trimethylsilyl)imidazole.

8. A process according to claim 2, wherein the anhydrous aprotic polar solvent of silylation step (a) is selected from the group consisting of N,N-dimethylformamide, N,N-dimethylacetamide, acetonitrile or tetrahydrofuran or a mixture thereof.

9. A process according to claim 1, wherein the recovered gabapentin of formula (1) is in an anhydrous or an hydrated form.

10. A process according to claim 1, wherein the gabapentin of formula (1) is recovered from the reaction mixture and crystallized by adding methanol, isopropanol or a mixture thereof.

11. A process according to claim 1, wherein the isolated gabapentin of formula (1) is gabapentin form II.

* * * * *